US00PP18799P2

(12) United States Plant Patent

Seidler

(10) Patent No.: US PP18,799 P2

(45) Date of Patent: May 6, 2008

(54) *HYPERICUM* PLANT NAMED 'SEICOL'

(50) Latin Name: *Hypericum androsaemum*
Varietal Denomination: Seicol

(76) Inventor: Thomas Seidler, DE-25337 Elmshorn, Ramskamp 64 (DE)

( * ) Notice: Subject to any disclaimer, the term of this patent is extended or adjusted under 35 U.S.C. 154(b) by 0 days.

(21) Appl. No.: 11/642,188

(22) Filed: Dec. 20, 2006

(51) Int. Cl.
*A01H 5/00* (2006.01)

(52) U.S. Cl. ..... Plt./442

(58) Field of Classification Search ..... Plt./442, Plt./263
See application file for complete search history.

(56) References Cited

PUBLICATIONS

UPOV ROM GTITM Computer Database, GTI Jouve Retrieval Software 2007/02 Citation for 'Seicol'.*

* cited by examiner

*Primary Examiner*—Wendy C. Haas
(74) *Attorney, Agent, or Firm*—Audrey Charles

(57) ABSTRACT

A new and distinct cultivar of *Hypericum* plant named 'Seicol', characterized by its yellow-colored flowers, large, dark red orange-colored fruit, dark green-colored foliage, and vigorous, upright growth habit.

1 Drawing Sheet

Latin name of genus and species of plant claimed: *Hypericum androsaemum.*
Variety denomination: 'Seicol'.

BACKGROUND OF THE INVENTION

The present invention relates to a new and distinct cultivar of *Hypericum* plant botanically known as *Hypericum androsaemum,* used commercially as stems with fruit and hereinafter referred to by the cultivar name 'Seicol'.

The new cultivar originated in a controlled breeding program in Elmshorn, Germany during July 2001. The objective of the breeding program was the development of *Hypericum* cultivars with unique and large attractive fruit coloration.

The new *Hypericum* cultivar is the result of open-pollination using a bulk of proprietary female and male *Hypericum androsaemum* parent plants, not patented, characterized by large brown-colored berries or small berries ranging in color from red to pink. The new cultivar was discovered and selected as a single flowering plant within the progeny of the above stated open-pollination during June 2002 in a controlled environment in Elmshorn, Germany.

Asexual reproduction of the new cultivar by terminal stem cuttings since June 2002 at Elmshorn, Germany and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Seicol' as a new and distinct cultivar of *Hypericum* plant:

1. Yellow-colored flowers;
2. Large, dark red orange-colored fruit
3. Dark green-colored foliage; and
4. Vigorous, upright growth habit.

Plants of the new cultivar differ from plants of the female and male parents primarily in fruit size and coloration.

Of the many commercially available *Hypericum* cultivars known to the inventor, the most similar in comparison to the new cultivar is 'Excellent Flair', not patented. However, in side by side comparisons, plants of the new cultivar differ from plants of 'Excellent Flair' in the following characteristics:

1. Plants of the new cultivar are shorter than plants of 'Excellent Flair';
2. Plants of the new cultivar have smaller leaves than plants of 'Excellent Flair'; and
3. Plants of the new cultivar have smaller and fewer inflorescences than plants of 'Excellent Flair'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Seicol'. The plants were grown outdoors in 2-gallon size pots for 25 weeks at Arroyo Grande, Calif.

DETAILED BOTANICAL DESCRIPTION

Figure 1:
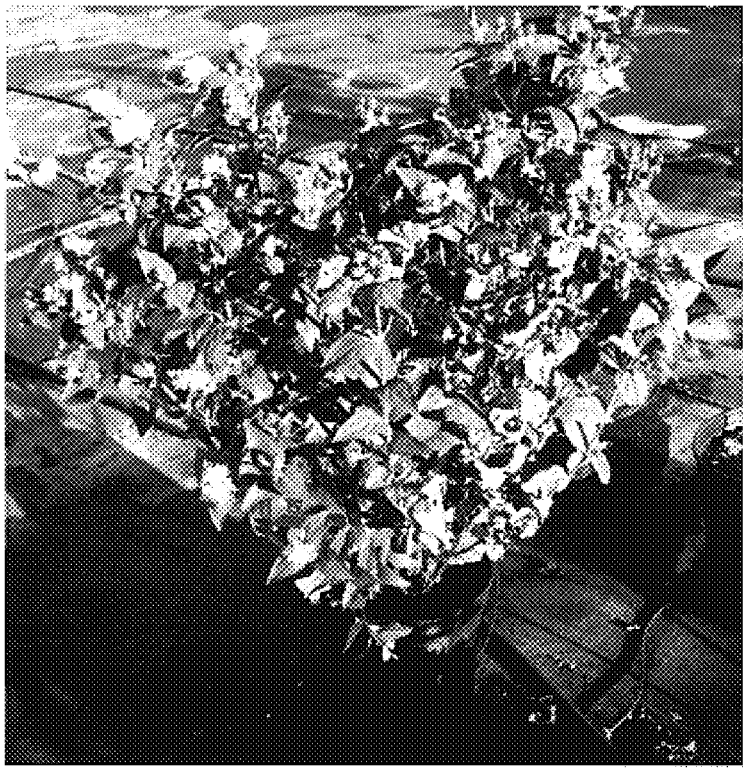
FIG. 1 illustrates a side view of flowers, fruits, and the overall growth habit of 'Seicol'.
Figure 2:
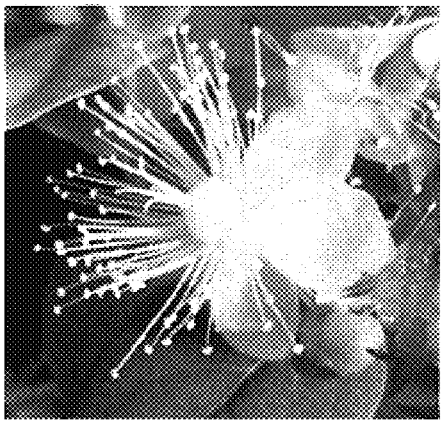
FIG. 2 illustrates a close-up view of the flower of 'Seicol'.
Figure 3:
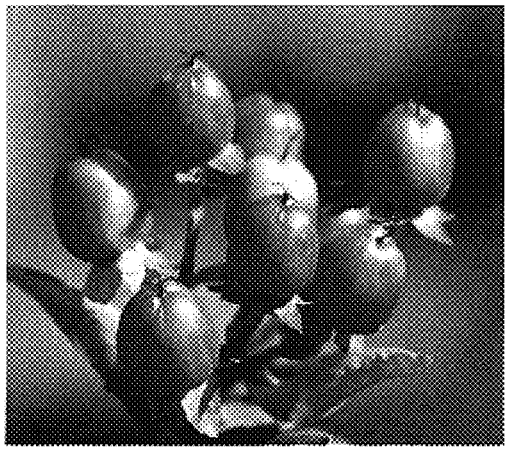
FIG. 3 illustrates a close-up view of the fruit of 'Seicol'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Aug. 18, 2004 between 10:00 a.m. and 12:00 p.m. under natural light conditions in Elmshorn, Germany when outdoor temperatures typically range from 82° F. (28° C.) during the day to 53° F. (12° C.) at night.

The following descriptions and measurements describe plants grown in an outdoor nursery in Elmshorn, Germany and under commercial production practices. Plants were about two years old.

Botanical classification: *Hypericum androsaemum* cultivar Seicol.

Parentage:

*Female parent.*—A proprietary mix of *Hypericum androsaemum* plants, not patented.

*Male parent.*—A proprietary mix of *Hypericum androsaemum* plants, not patented.

Propagation:

*Type cutting.*—Terminal stem.

*Time to initiate roots.*—Approximately 14 to 21 days.

*Time to produce a rooted cutting.*—Approximately 2 months.

*Root description.*—Fine, white.

*Rooting habit.*—Freely branching, dense. Height of entire root structure: Approximately 50 cm. Diameter of entire root structure: Approximately 100 cm.

Plant description:

*Form.*—Erect, perennial, woody shrub; broad, inverted triangle.

*Growth habit and general appearance.*—Vigorous, dense bushy.

*Size.*—Height from soil level to top of plant plane: Approximately 64 cm. Width: Approximately 50 to 60 cm.

*Branching habit.*—Freely basal branching. Quantity of lateral branches per plant: Approximately 19. Quantity of harvestable stems per year per plant: Approximately 14, production of stems increases with age of plant and remains constant after three years of growth.

*Branch.*—Shape: Rounded. Strength: Strong. Length: Approximately 64 cm. Diameter: Approximately 8.0 mm. Length of central internode: Approximately 5.8 cm. Texture: Smooth, glabrous. Color of mature stem: 177B.

Foliage description:

*General description.*—Quantity of leaves per main branch: Approximately 50. Form: Simple, sessile. Arrangement: Opposite.

*Leaves.*—Shape: Oval to lanceolate. Margin: Entire. Apex: Acute. Base: Cordate. Venation pattern: Pinnate. Length of mature leaf: Approximately 6.6 cm. Width of mature leaf: Approximately 3.1 cm. Texture of upper surface: Smooth, glabrous. Texture of lower surface: Smooth, glabrous. Color of upper surface of young foliage: 137C with venation of 144C. Color of lower surface of young foliage: 138B with venation of 144C. Color of upper surface of mature foliage: 139A with venation of 144C. Color of lower surface of mature foliage: 147B with venation of 144C.

Flowering description:

*Flowering habit.*—'Seicol' flowers throughout the summer under outdoor growing conditions and produces harvestable cut stems with fruit beginning in August; flowering period typically lasts about 60 days.

*Lastingness of individual flower on the plant.*—Approximately 14 days.

*Lastingness of individual flower as a cut flower.*—Approximately 12 days.

Inflorescence description:

*General description.*—Type: Compound umbel, not persistent. Quantity of flowers per inflorescence: Approximately 6. Fragrance: None. Length or height: Approximately 4.0 cm. Width: Approximately 5.5 cm.

*Peduncle.*—Strength: Strong. Aspect: Approximately 30° angle from stem. Length: Approximately 2.6 cm. Diameter: Approximately 2.0 mm. Texture: smooth, glabrous. Color: 144A with an overlay of 183C.

Flower description:

*General description.*—Type: Single, sessile. Aspect: Upright. Quantity per lateral stem: Approximately 40.

*Bud.*—Shape: Ovoid. Quantity per lateral stem: Approximately 40. Length: Approximately 9.0 mm. Diameter: Approximately 6.0 mm. Color: 14A.

*Corolla.*—Shape: Round. Diameter: Approximately 2.5 cm. Depth: Approximately 1.7 cm.

*Petals.*—Quantity: 5, nonimbricate. Shape: Oval. Appearance: Flat. Aspect: Slightly concave. Margin: Entire. Apex: Rounded. Base: Attenuate. Length: Approximately 1.5 cm. Width: Approximately 9.8 mm. Texture of upper and lower surfaces: Smooth, glabrous. Color of upper surface when first open: 13A. Color of lower surface when first open: 12A. Color of upper surface when fully open: 13A fades to 12A with age. Color of lower surface when fully open: 13B.

*Calyx.*—Shape: Divergate. Length: Approximately 8.0 mm. Width: Approximately 1.8 cm.

*Sepals.*—Quantity per flower: 5, nonimbricate. Shape: Oval. Appearance: Flat. Margin: Entire. Apex: Apiculate. Base: Broadly cunerate. Length: Approximately 8.4 mm. Width: Approximately 4.8 mm. Texture of upper and lower surfaces: Smooth, glabrous. Color of upper surface of immature sepals: 144A. Color of lower surface of immature sepals: 144B. Color of upper and lower surfaces of mature sepals: 59A.

*Reproductive organs.*—Androecium: Stamen quantity: Approximately 85. Anther shape: Oval. Anther length: Approximately 0.5 mm. Anther color: 17C. Pollen amount: Moderate. Pollen color: 13B. Gynoecium: Pistil quantity: 3 per flower. Pistil length: Approximately 7.0 mm. Stigma shape: Globular. Stigma color: 59A. Style length: Approximately 6.0 mm. Style color: 150C. Ovary color: 150B.

*Fruit.*—Type: Capsule. Taste: Bitter. Shape: Ellipsoidal. Quantity per lateral branch: Approximately 40. Quantity per plant: Greater than 500. Days to ripening: Approximately 10 days to color and 30 days to seed. Longevity on plant: Approximately 30 days. Length: Approximately 1.3 cm. Diameter: Approximately 1.1 cm. Texture: Smooth, glabrous. Color: 42B.

*Seed.*—Quantity per fruit: Typically more than 100. Length: Approximately 1.0 mm. Diameter: Approximately 0.5 mm. Texture: Smooth, glabrous. Color: 200D.

Disease and pest resistance: Plants of the new *Hypericum* have been observed to be resistant to rust.

Weather tolerance: Plants of the new *Hypericum* have been observed to tolerate temperatures ranging from −10° C. to 35° C., and to demonstrate tolerance to rain and wind effects.

What is claimed is:

1. A new and distinct cultivar of *Hypericum* plant named 'Seicol', substantially as herein shown and described.

* * * * *